(12) United States Patent
Sharma (10) Patent No.: US 8,807,538 B2
(45) Date of Patent: Aug. 19, 2014

(54) CENTRIFUGAL FAN DEVICE

(75) Inventor: Nitin Sharma, Kenosha, WI (US)

(73) Assignee: S.C. Johnson & Son, Inc., Racine, WI (US)

( * ) Notice: Subject to any disclaimer, the term of this patent is extended or adjusted under 35 U.S.C. 154(b) by 24 days.

(21) Appl. No.: 13/494,899

(22) Filed: Jun. 12, 2012

(65) Prior Publication Data

US 2012/0275932 A1 Nov. 1, 2012

Related U.S. Application Data

(63) Continuation of application No. 13/096,527, filed on Apr. 28, 2011.

(51) Int. Cl.
*B01F 3/04* (2006.01)
*A61L 9/12* (2006.01)
*A01M 1/20* (2006.01)

(52) U.S. Cl.
CPC ............ *A61L 9/122* (2013.01); *A01M 1/2033* (2013.01); *A01M 1/2044* (2013.01); *A61L 9/127* (2013.01); *Y10S 261/88* (2013.01)
USPC ...... 261/30; 261/104; 261/107; 261/DIG. 88; 422/124; 329/57

(58) Field of Classification Search
USPC ............ 261/30, 104, 107, DIG. 88; 422/124; 239/57; 392/386, 395
See application file for complete search history.

(56) References Cited

U.S. PATENT DOCUMENTS

| | | |
|---|---|---|
| 2,562,589 A | 7/1951 | Uttz |
| 3,747,902 A | 7/1973 | Bailey |
| 3,829,071 A | 8/1974 | Valbona et al. |
| 4,035,451 A | 7/1977 | Tringali |
| 4,064,203 A | 12/1977 | Cox |
| 4,166,087 A | 8/1979 | Cline et al. |
| 4,271,092 A | 6/1981 | Sullivan et al. |
| 4,383,951 A | 5/1983 | Palson |
| 4,396,557 A | 8/1983 | DeLuca |
| 4,432,938 A | 2/1984 | Meetze, Jr. |
| 4,707,338 A | 11/1987 | Spector |
| 4,739,928 A | 4/1988 | O'Neil |
| 5,431,885 A | 7/1995 | Zlotnik |

(Continued)

FOREIGN PATENT DOCUMENTS

| | | |
|---|---|---|
| AU | 2939777 A | 4/1979 |
| EP | 0423816 A2 | 4/1991 |

(Continued)

OTHER PUBLICATIONS

PCT/US2013/045337 International Search Report and Written Opinion, dated Dec. 10, 2013.

(Continued)

*Primary Examiner* — Robert A Hopkins (57) ABSTRACT

A dispensing device includes a housing, a fan, and an annular reservoir. A compound is disposed within the reservoir. The dispensing device further includes a permeable substrate in communication with the annular reservoir for releasing the compound in a first passive state. The compound is released from the permeable substrate according to a uniform diffusion profile. Rotation of the fan causes air to pass over the permeable substrate to release the compound in a second active state.

18 Claims, 10 Drawing Sheets

(56) References Cited

U.S. PATENT DOCUMENTS

| | | | |
|---|---|---|---|
| 5,480,591 A | 1/1996 | Lagneaux et al. |
| 5,498,397 A | 3/1996 | Horng |
| 5,662,835 A | 9/1997 | Collingwood |
| 5,970,643 A | 10/1999 | Gawel, Jr. |
| 6,179,275 B1 | 1/2001 | Lagneaux et al. |
| 6,371,450 B1 | 4/2002 | Davis et al. |
| 6,569,387 B1 | 5/2003 | Furner et al. |
| 6,632,405 B2 | 10/2003 | Lua |
| 6,713,024 B1 | 3/2004 | Arnell et al. |
| 6,769,631 B2 | 8/2004 | Brown |
| 7,040,548 B2 | 5/2006 | Rodgers |
| 7,040,561 B2 | 5/2006 | Wong et al. |
| 7,167,641 B2 | 1/2007 | Tam et al. |
| 7,175,815 B2 | 2/2007 | Yamasaki et al. |
| 7,341,698 B2 | 3/2008 | Pedrotti et al. |
| 7,382,975 B2 | 6/2008 | Caserta et al. |
| 7,499,632 B2 * | 3/2009 | Granger et al. | 392/386 |
| 7,744,833 B2 | 6/2010 | Varanasi et al. |
| 7,748,687 B2 | 7/2010 | Pankhurst et al. |
| 7,840,123 B2 | 11/2010 | Belongia et al. |
| 7,857,236 B2 | 12/2010 | Zlotnik et al. |
| 2006/0043619 A1 | 3/2006 | Brown et al. |
| 2006/0074742 A1 | 4/2006 | Santandrea |
| 2006/0153731 A1 | 7/2006 | Brown et al. |
| 2007/0036673 A1 | 2/2007 | Selander |
| 2007/0127249 A1 | 6/2007 | Medley et al. |
| 2007/0217771 A1 | 9/2007 | Granger et al. |
| 2007/0257130 A1 | 11/2007 | Butler et al. |
| 2007/0280653 A1 | 12/2007 | Viera |
| 2008/0164337 A1 | 7/2008 | Brown et al. |
| 2008/0292508 A1 | 11/2008 | Zlotnik et al. |
| 2008/0305002 A1 | 12/2008 | Bertassi et al. |
| 2008/0311008 A1 | 12/2008 | Tranzeat |
| 2008/0315006 A1 | 12/2008 | Belongia et al. |
| 2009/0162253 A1 | 6/2009 | Porchia et al. |
| 2009/0185951 A1 | 7/2009 | Litten-Brown et al. |
| 2009/0200393 A1 | 8/2009 | Avelar |
| 2010/0044453 A1 | 2/2010 | Porchia et al. |
| 2010/0051598 A1 | 3/2010 | Butler et al. |
| 2010/0059601 A1 | 3/2010 | Bankers et al. |
| 2010/0086448 A1 | 4/2010 | Faber et al. |
| 2010/0116898 A1 | 5/2010 | Litten-Brown et al. |
| 2010/0143203 A1 | 6/2010 | Miro Amenos et al. |
| 2010/0150774 A1 | 6/2010 | Marchetti et al. |
| 2011/0027124 A1 | 2/2011 | Albee et al. |

FOREIGN PATENT DOCUMENTS

| | | |
|---|---|---|
| EP | 0672425 A1 | 9/1995 |
| EP | 1262100 A1 | 12/2002 |
| JP | 201102927 A | 2/2011 |
| WO | 2007109504 A2 | 9/2007 |
| WO | 2010112895 A1 | 10/2010 |
| WO | 2011019404 A2 | 2/2011 |
| WO | WO2012149114 A1 | 11/2012 |

OTHER PUBLICATIONS

PCT/US2012/035130 International Search Report dated Jul. 9, 2012.

* cited by examiner

CENTRIFUGAL FAN DEVICE

CROSS REFERENCE TO RELATED APPLICATIONS

This application is a continuation-in-part of U.S. patent application Ser. No. 13/096,527 filed on Apr. 28, 2011.

REFERENCE REGARDING FEDERALLY SPONSORED RESEARCH OR DEVELOPMENT

Not applicable

SEQUENTIAL LISTING

Not applicable

BACKGROUND OF THE DISCLOSURE

1. Field of the Disclosure

The present invention is directed to a centrifugal fan device and, in particular, a centrifugal fan device which is adapted for delivering a fragrance or an insecticide to an environment during use.

2. Description of the Background of the Disclosure

Many devices and apparatuses have been developed for delivering a fragrance (such as an air freshener) or insecticide (for example, citronella) to an environment of use. Some devices disseminate the fragrance or insecticide (collectively referred to as a compound) using passive means. Examples of devices with passive means include devices having a compound evaporate from a substrate or membrane which disseminate the compound into the environment. Other passive devices have a reservoir which contains a compound which is released into the environment as the compound evaporates.

In addition to the aforementioned passive devices, active devices have been developed to aid in the dissemination of the compound. Some active devices have fans which enhance the dissemination of a compound from either a substrate, membrane or reservoir. Still other devices have a heat source, separately or in combination with a fan, to disseminate the compound into the environment.

There is a need in the art for an improved apparatus for enhanced compound delivery.

SUMMARY OF THE INVENTION

According to one embodiment, a dispensing device includes a housing, a fan, and an annular reservoir. A compound is disposed within the reservoir. The dispensing device further includes a permeable substrate in communication with the annular reservoir for releasing the compound in a first passive state. The compound is released from the permeable substrate according to a uniform diffusion profile. Rotation of the fan causes air to pass over the permeable substrate to release the compound in a second active state.

According to another embodiment, a refill includes an annular reservoir having a compound disposed therein and an annular permeable substrate in communication with the compound. The permeable substrate includes a horizontal surface having at least one wick extending from the horizontal surface into the annular reservoir.

According to a different embodiment, a refill includes an annular reservoir having a compound disposed therein and at least on wick extending from the annular reservoir.

The above and other aspects of the present invention will be apparent from the following description of the preferred embodiments of the invention and from the accompanying drawings.

DETAILED DESCRIPTION OF THE DRAWINGS

Figure 1:
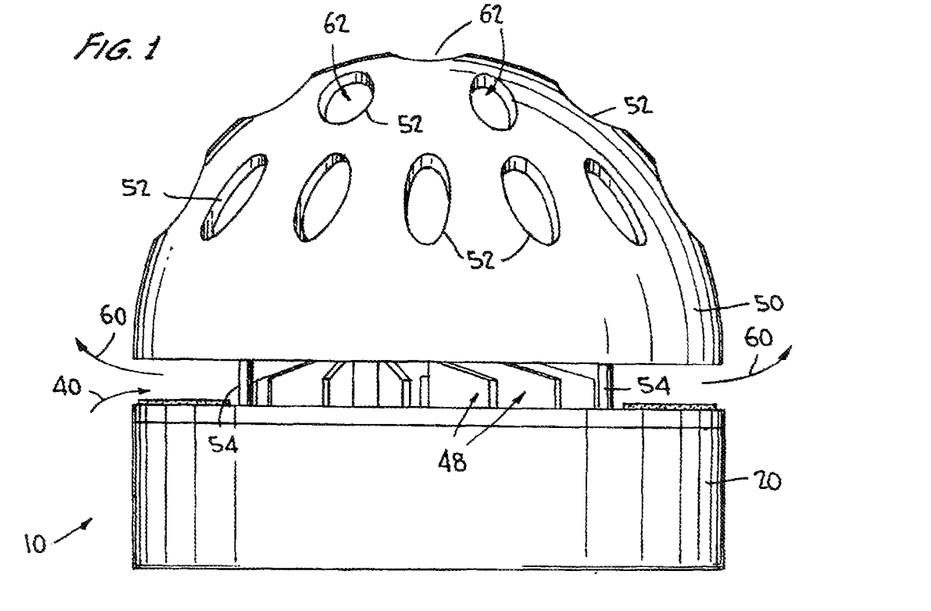
FIG. 1 is an elevational view of a centrifugal fan device, in accordance with one embodiment of the present invention.
Figure 2:
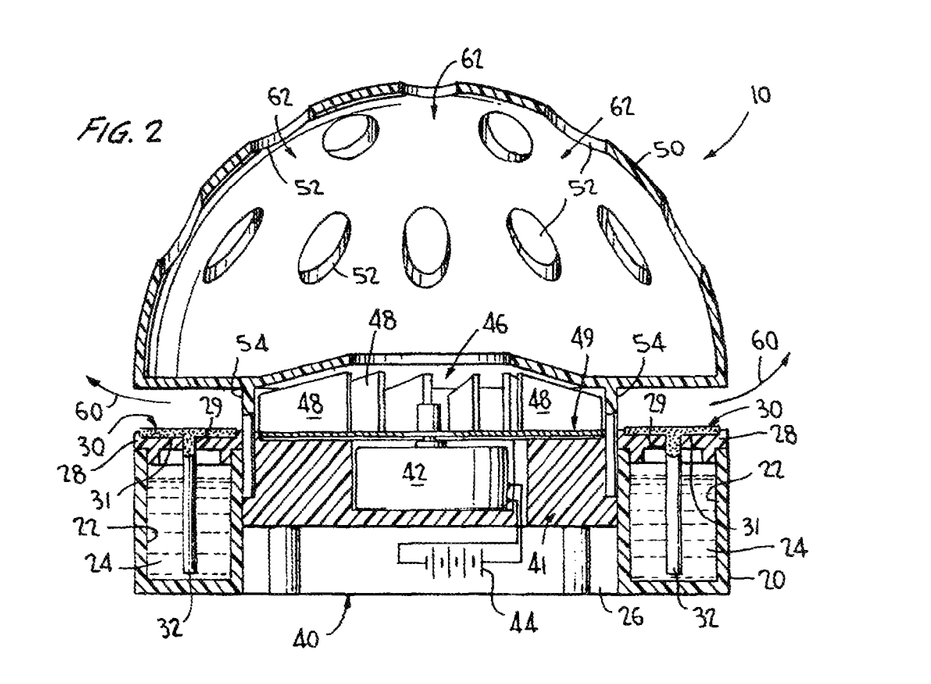
FIG. 2 is a cross-sectional view of the centrifugal fan device of FIG. 1.

Referring generally to FIGS. 1, 2, 5, and 6, and, in particular to FIGS. 1 and 2, one embodiment of a centrifugal fan device 10 includes a base 20, a compound permeable substrate 30, a fan assembly 40 and a cover 50.

The base 20 has an annularly shaped reservoir 22 into which a compound 24 is disposed. The compound 24 may include a fragrance, insecticide, odor eliminator, or any other substance known to those skilled in the art capable of being emitted from the reservoir 22 as described in further detail below. The annularly shaped reservoir 22 defines a cylindrically shaped center cavity 26 into which the fan assembly 40 is disposed. A cap, such as plug 28, has a complementary annular shape to that of the reservoir 22, which completely covers the reservoir 22. Although the base 20 of device 10 is annularly shaped, the base can be triangular, rectangular, pentagonal, etc.

The compound permeable substrate 30 is advantageously annularly shaped, and is adapted to be disposed over the plug 28. A plurality of wicks 32 extend from a horizontal surface 31 into the reservoir 22 and are, thus, in contact with the compound 24. A series of bores 29 in the plug 28 are of a sufficient size to allow the wicks 32 to extend down from the horizontal surface 31, through the plug 28, to the reservoir 22 below. As a result, the compound 24 is able to be wicked from the reservoir 22 up the plurality of wicks 32 to the horizontal surface 31.

The fan assembly 40 includes a housing 41 which contains an electric motor 42 and batteries 44, although other means for powering the electric motor may be used. Further, the fan assembly 40 includes a centrifugal fan 46. The centrifugal fan 46 further comprises a plurality of fan blades 48. Advantageously, a base 49 of the centrifugal fan 46 is approximately at the same level as a horizontal surface 31 of the compound permeable substrate 30.

Figure 5:
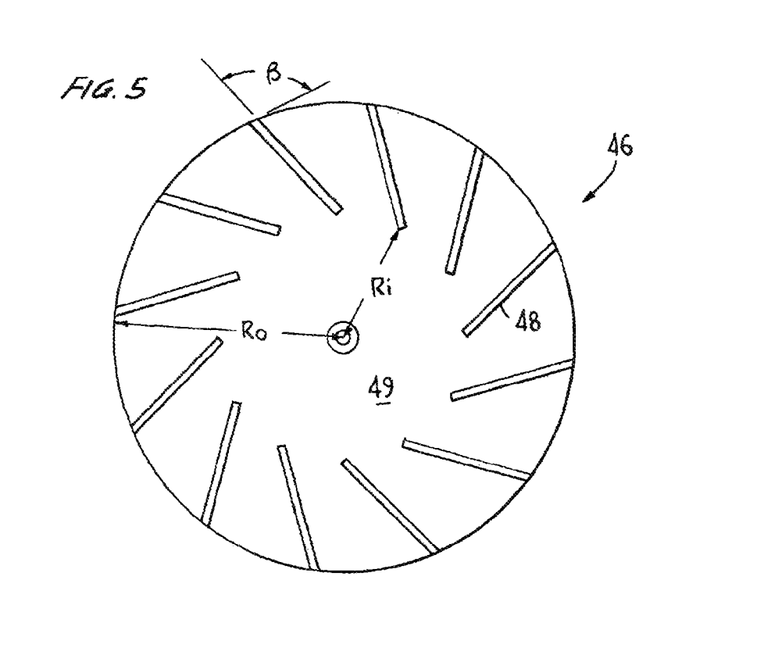
FIG. 5 is a top plan view of a centrifugal fan of the respective devices in FIGS. 1 and 3.
Figure 6:
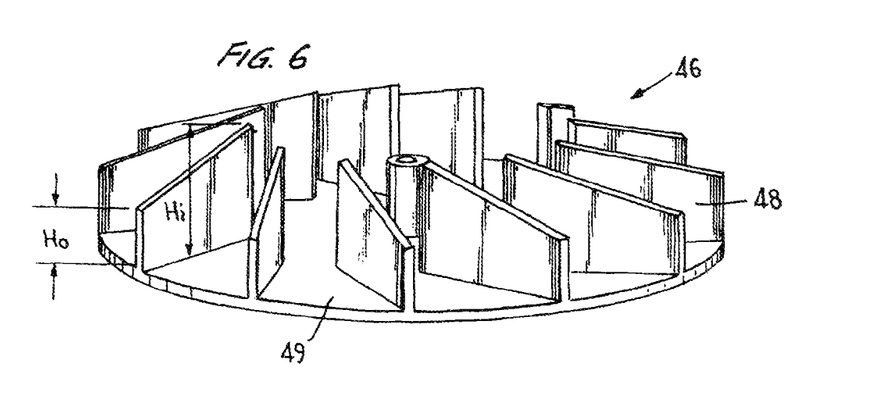
FIG. 6 is a perspective view of the centrifugal fan of FIG. 5.
Figure 7:
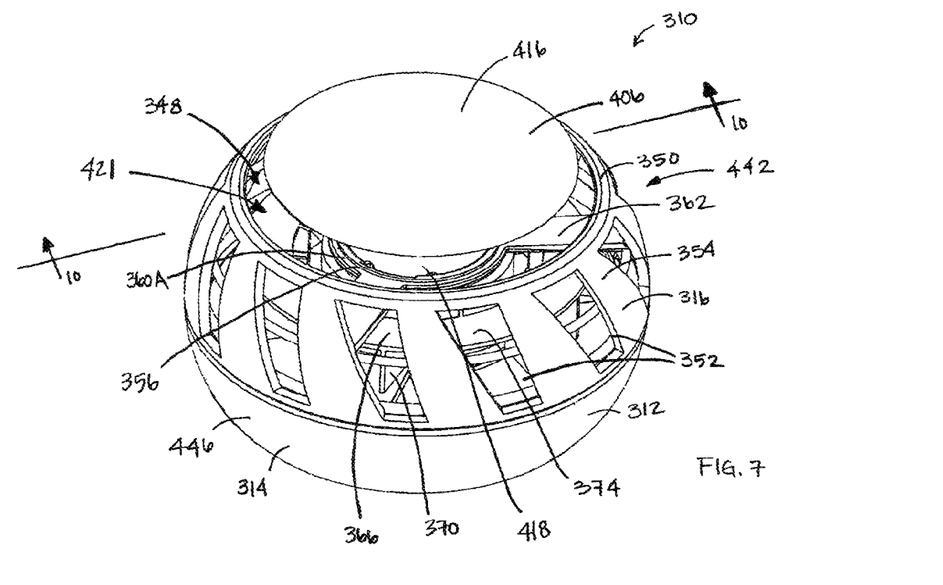
FIG. 7 is an isometric view of a further embodiment of a centrifugal fan device.
Figure 8:
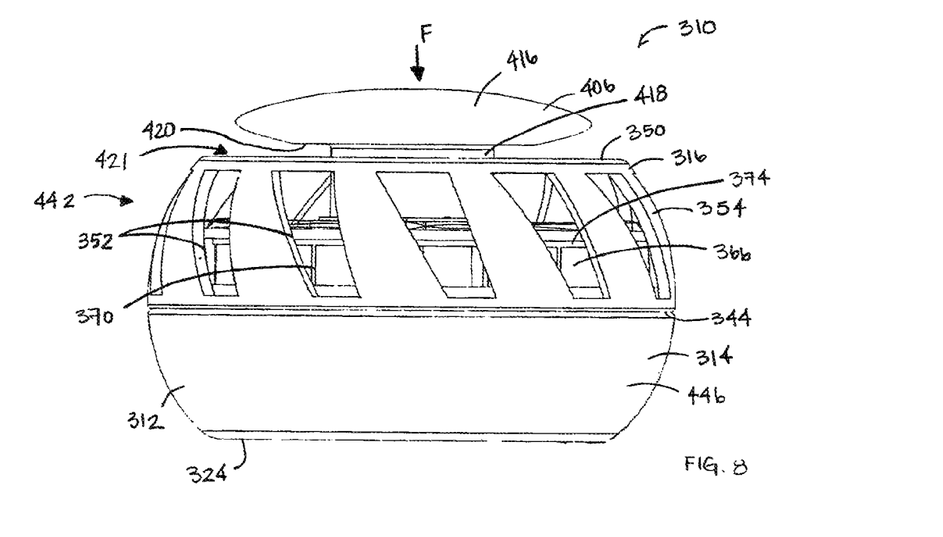
FIG. 8 is a front elevational view of the centrifugal fan device of FIG. 7.

Advantageously, the electric motor 42 propels the centrifugal fan 46 with RPMs between 100 and 4,000 and, preferably, between 200 and 600 RPMs. Further, advantageously, the centrifugal fan 46 has between 5 and 15 blades 48 and, preferably, between 10 and 14 blades. The centrifugal fan 46 has a fan blade outlet angle ($\beta$) between 30° and 150° and, preferably, between 90° and 145°. The centrifugal fan 46 has a fan blade inner height (Hi) between 5 mm and 15 mm and, preferably, between 9 mm and 12 mm, and has a fan blade outlet height (Ho) between 20% and 100% of the fan blade inlet height and, preferably, 50% of the inlet height. The centrifugal fan 46 has a fan blade inner radius (Ri) between 5 mm and 15 mm and a fan blade outer radius (Ro) of greater than or equal to ($\geq$) 20 mm. Although the plurality of blades 48 are shown as straight, it is contemplated that curved blades may also be used.

The cover 50 is disposed over the centrifugal fan 46. The cover comprises a plurality of apertures 52. The cover 50 provides for a side air passage from the centrifugal fan 46 to the outside environment, as identified by arrows 60. In one advantageous form, the passage is provided by a gap between the cover 50 and the base 20. The cover 50 is attached to the base 20 using a plurality of legs 54.

During use of the centrifugal fan device 10, the electric motor 42, powered by batteries 44, drives the centrifugal fan 46 to rotate, thereby drawing air in from the environment through the apertures 52 in the cover 50, as indicated by arrow 62. The air continues axially downward to the centrifugal fan 46. Then, the centrifugal fan 46 forces the air over the horizontal surface 31 of the compound permeable substrate 30 and, finally, the air exits the device 10 through the gap between the cover 50 and base 20, as identified by arrows 60.

Since the centrifugal fan 46 is substantially at the same height as a horizontal surface 31, and it directly forces air across the surface, the size of the horizontal surface 31 is minimized, as compared to the size it would have to be to achieve the same compound dispersement were the fan not at the same height as the substrate.

In addition, the centrifugal fan device 10 allows for a 360 degree dispersion of a compound 24 using the centrifugal fan 46, which draws air axially downward, in towards a center of the device, and blows air radially 360 degrees over a compound permeable substrate 30, which, as a result, becomes an evaporating surface.

Although the reservoir 22 is located below the centrifugal fan 46 in device 10, a reservoir and compound permeable substrate can be located above the centrifugal fan, e.g., in the cover section of the device.

Figure 3:
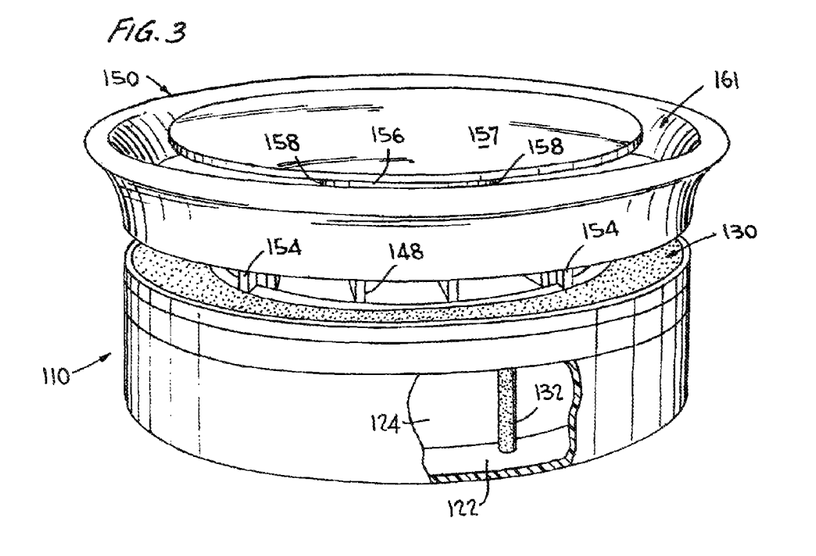
FIG. 3 is a perspective view of a centrifugal fan device, in accordance with another embodiment of the present invention, with a partial cutaway portion of a base thereof.
Figure 4:
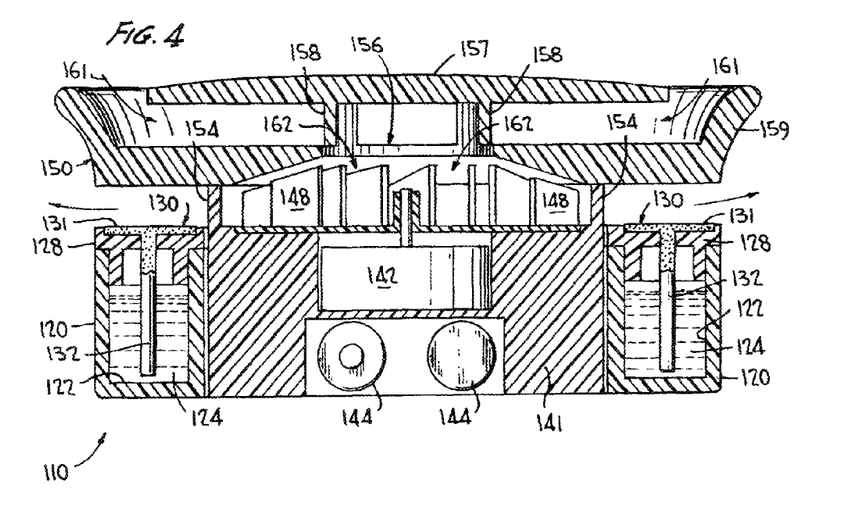
FIG. 4 is a cross-sectional view of the centrifugal fan device of FIG. 3.

Referring now to FIGS. 3 and 4, where like elements to those in FIGS. 1 and 2 have been increased by 100, centrifugal fan device 110 represents an alternative embodiment which is essentially the same as that of centrifugal fan device 10, except for having a different cover. Accordingly, various elements, which are the same as those in centrifugal fan device 10, are not specifically repeated here, as they are essentially the same as those in centrifugal fan device 10.

Cover 150 comprises a disc 157 which is disposed over aperture 156. A plurality of legs 158 attach the disc 157 to a main portion 159 of the cover. During use of the centrifugal fan device 110, when the centrifugal fan motor 142 is energized, thereby causing the centrifugal fan 146 to spin, air is drawn in from the environment between the disc 157 and a main portion of the cover 159, as indicated by arrow 161. Air continues through the aperture 156, as indicated by arrow 162, and is then blown radially 360 degrees over the horizontal surface 131 of the compound permeable substrate 130, which thereby acts as an evaporating surface for the compound 124.

FIGS. 7-15 illustrate an additional embodiment of a centrifugal fan device 310 that is activated by a manual drive mechanism as opposed to an electric motor. The centrifugal fan device 310 includes a housing 312 comprising a base 314 and a cover 316. A fan assembly 318 and a manual drive mechanism 320 are disposed within the housing 312. The base 314 is generally bowl shaped and includes a circular aperture 322 disposed in a bottom 324 of the base 314. An annularly shaped refill 326 is disposed within the base 314. The refill 326 includes an annularly shaped reservoir 328 into which a liquid compound 330 is disposed. It is contemplated that the reservoir 328 and base 314 may be a single component. Indeed, various alternative embodiments of the refill are discussed in greater detail hereinbelow.

Figure 11:
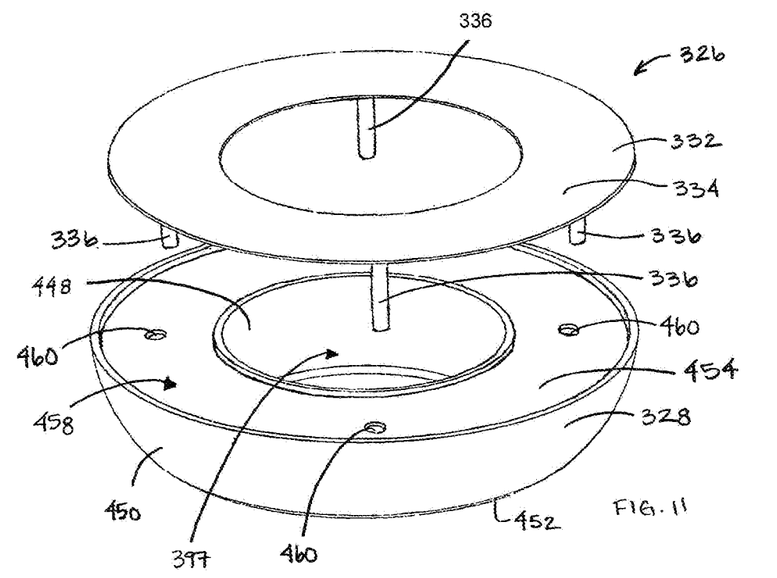
FIG. 11 is an exploded isometric view of a reservoir and substrate for use in the centrifugal fan device of FIG. 7.

Referring more particularly to FIG. 11, the refill 326 further includes an annularly shaped permeable substrate 332, which is adapted to be in fluid communication with the reservoir 328. In the present embodiment, the permeable substrate 3.32 includes a horizontal surface 334 having a plurality of wicks 336 extending therefrom. The horizontal surface 334 is substantially parallel to a top surface 330A of the liquid compound 330 disposed in the reservoir 328. The plurality of wicks 336 extend from the horizontal surface 334 into the reservoir 328, thereby putting the horizontal surface 334 of the permeable member 332 in communication with the liquid compound 330. The horizontal surface 334 and the plurality of wicks 336 are made of a liquid permeable material, which allows the liquid compound 330 to be absorbed therein. For example, in a preferred embodiment, the horizontal surface 334 and the wicks 336 are preferably made of a porous plastic such as polyethylene, polypropylene, polyvinylidene fluoride, and polycarbonate. The horizontal surface 334 and the wicks 336 of the liquid permeable substrate may also be made .of bonded capillary structures that are made of polymeric fibers bonded together. Materials used to make these bonded capillary structures include polyester, polyolefins, nylon, cellosics, acetate, and other fibers. It is contemplated that the wick may be made out of other materials capable of absorbing the liquid compound. Further, the horizontal surface 334 and the wicks 336 may be separate pieces or they may be made integral.

Figure 9:
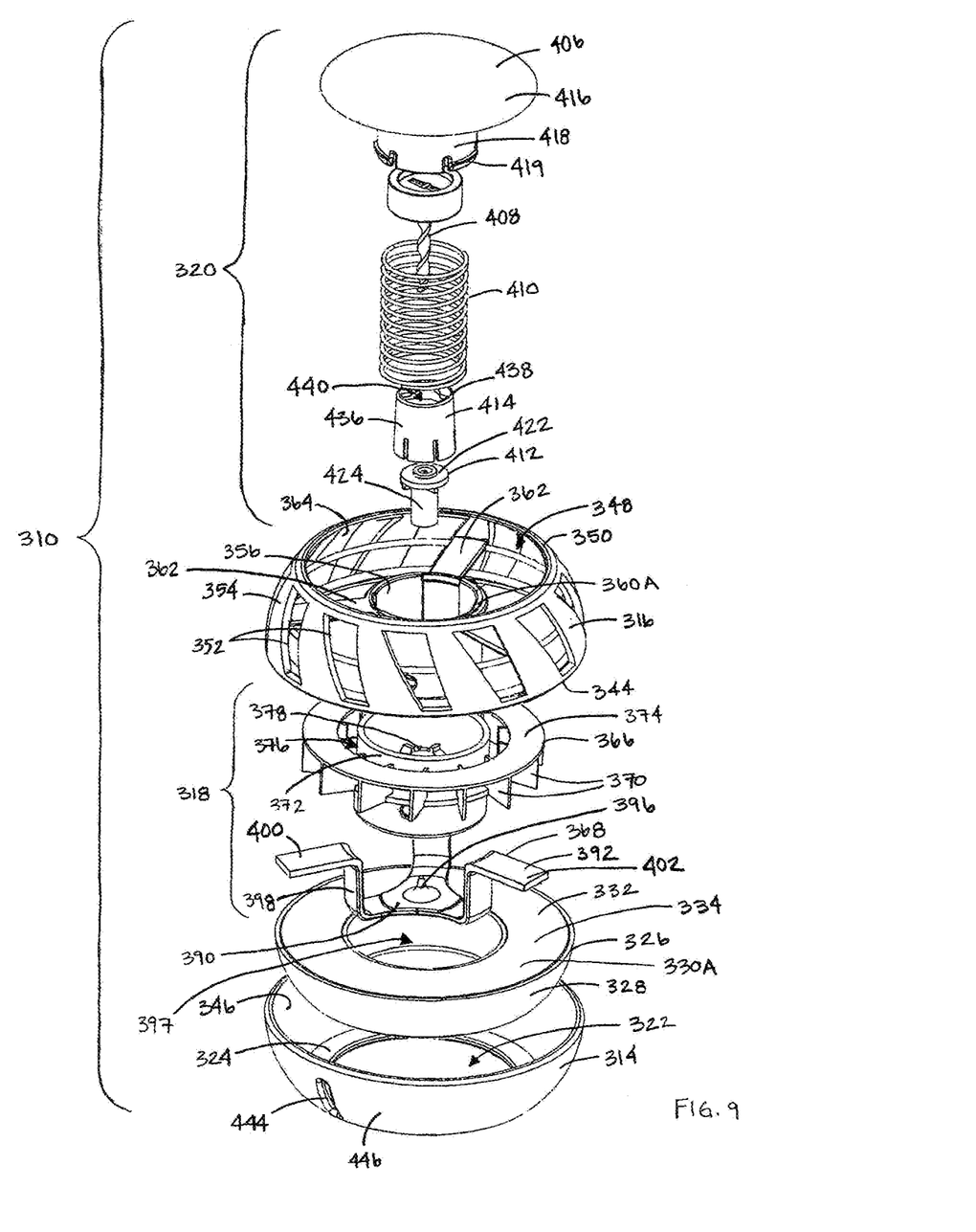
FIG. 9 is an exploded isometric view of the centrifugal fan device of FIG. 7.
Figure 10:
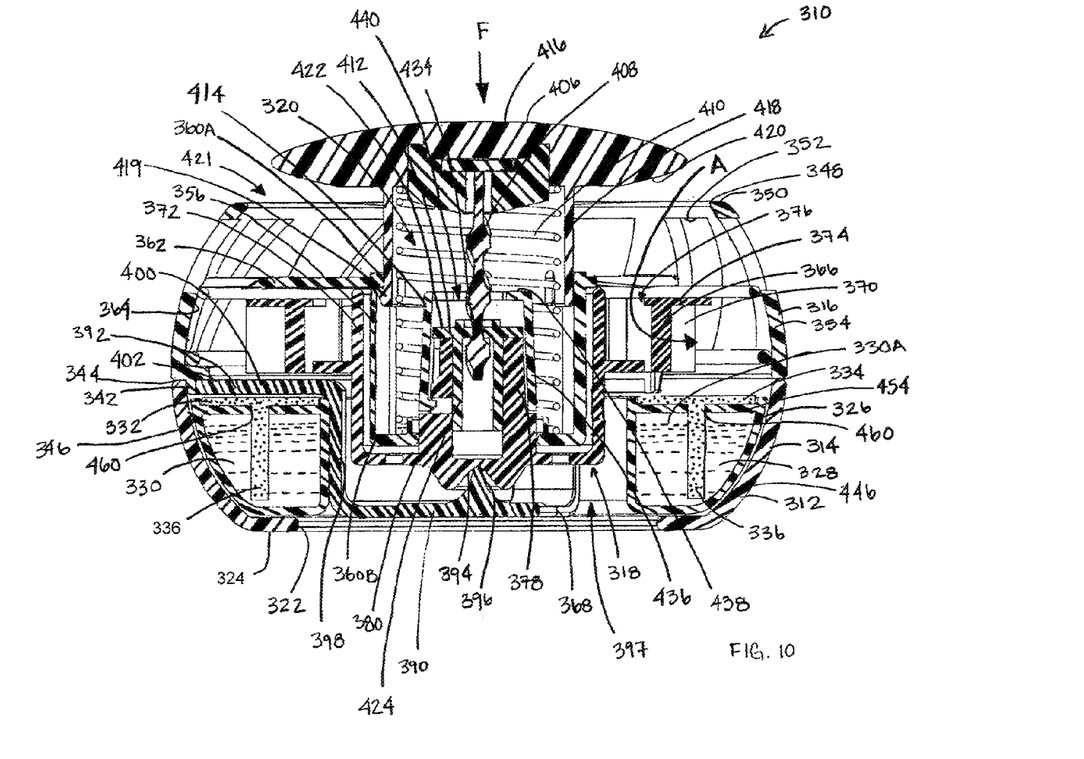
FIG. 10 is a cross-sectional view of the centrifugal fan device of FIG. 7 taken generally along the line 10-10 of FIG. 7.

With reference again to FIGS. 7-10 and 12, the cover 316 is adapted for interlining relationship with the base 314. The cover 316 includes a plurality of feet 342 depending from a lower edge 344 thereof (see FIG. 10). The feet 342 are capable of frictionally engaging with an inner sidewall 346 of the base 314 to prevent the cover 316 from releasing from the base 314 or rotating during use. Other connections known to those of skill in the art may also be used to releasably attach the cover 316 to the base 314. FIGS. 9 and 10 show that the cover 316 also includes an aperture 348 disposed in an upper end 350 thereof. Further, a plurality of vents 352 are disposed in a sidewall 354 of the cover 316, which allow air laden with the compound 330 to exit the device 310.

With reference still to FIGS. 9 and 10, the cover 316 further includes a cylindrical support 356 suspended within the cover 316. The cylindrical support 356 has open upper and lower ends 360A, 360B, respectively, and is suspended within the cover 316 by three arms 362, which extend from an inner sidewall 364 of the cover 316 to the cylindrical support 356. The cylindrical support 356 is adapted to help support and retain the fan assembly 318 and drive mechanism 320 within the housing 312.

Figure 12:
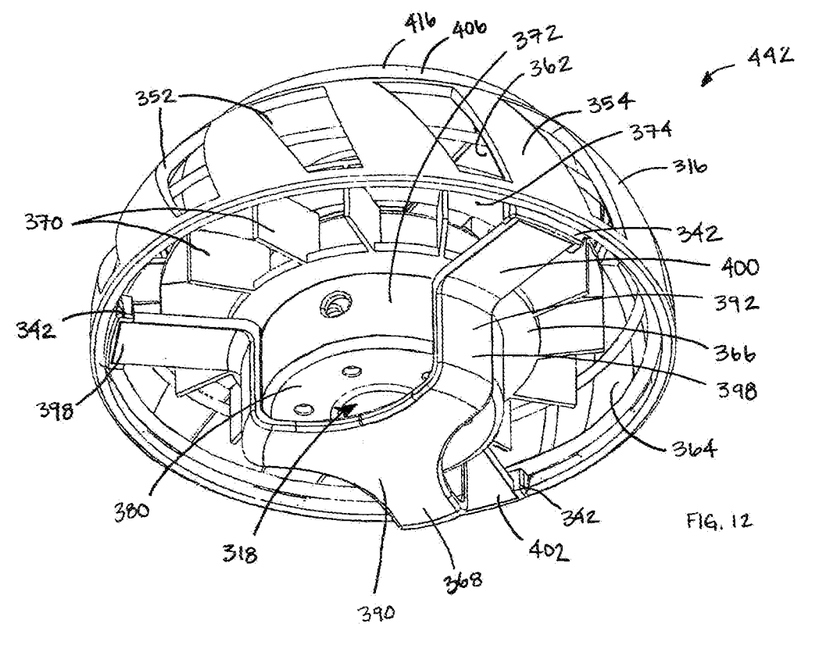
FIG. 12 is an isometric view of a bottom, front, and side of the centrifugal fan device of FIG. 7, wherein a reservoir and a bottom have been omitted.
Figure 15:
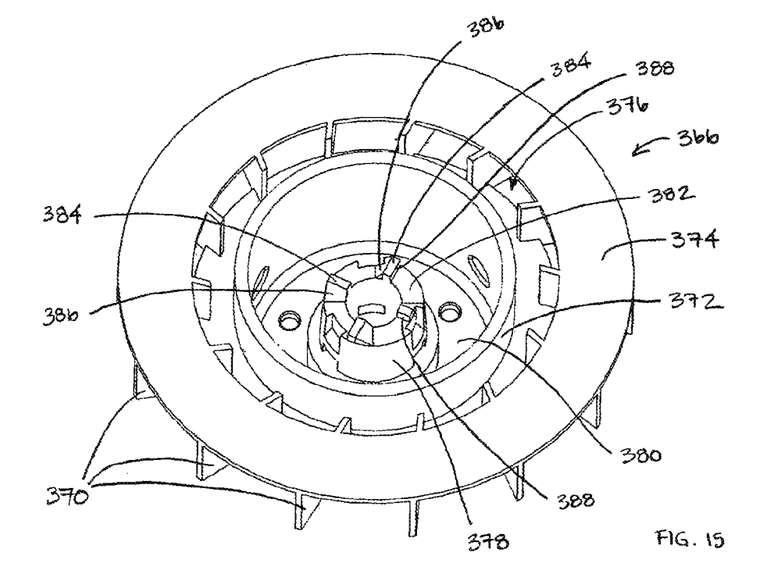
FIG. 15 is an isomeric view of a centrifugal fan for use in the centrifugal fan device of FIG. 7.

Turning to FIGS. 9, 10 and 12, the fan assembly 318 generally includes a centrifugal fan 366 and a pivot 368. The centrifugal fan 366 includes a plurality of fan blades 370 extending from a central barrel 372 thereof. FIGS. 9, 10, and 15 illustrate that an annular plate 374 connects and covers an outer portion of the plurality of fan blades 370. A gap 376 formed between the annular plate 374 and the barrel 372 allows air to be drawn into the fan 366 as described in further detail below. The barrel 372 is shaped to receive the cylindrical support 356 of the cover 316 when the device 310 is assembled. As shown in FIG. 15, the fan 366 further includes a cylindrically shaped axle 378 that is located within the barrel 372 and extends upwardly from a bottom end 380 thereof. An upper end 382 of the axle 378 includes a plurality of teeth 384. The teeth 384 include sloped first sides 386 and vertical second sides 388.

Referring again to FIGS. 9, 10 and 12, the pivot 368 includes a bottom portion 390 and a plurality of arms 392 extending from the bottom portion 390. Turning to FIG. 10, the barrel 372 of the fan 366 is received within the arms 392 of the pivot 368. A groove 394 located on the bottom end 380 of the barrel 372 rests on a cone-shaped projection 396 extending from the bottom 390 of the pivot 368. The cone-shaped projection 396 acts as a pivot point about which the fan 366 rotates within the device 310.

Referring to FIGS. 9 and 10, the pivot 368 is designed to fit within a central cavity 397 of the annularly shaped refill 326 and base 314 when the device 310 is assembled. As shown in FIG. 12, the arms 392 include main portions 398 that extend upwardly from the bottom portion 390 of the pivot 368 and overhang portions 400 that extend outwardly approximately 90° from the main portions 398. The overhang portions 400 extend above the horizontal surface 334 of the permeable substrate 332 of the annular refill 326. Distal end portions 402 of the overhang portions 400 are received within the feet 342 of the cover 316 to prevent the pivot 368 from rotating when the fan 366 rotates. Receipt of the arms 392 of the pivot 368 within the feet 342 may be accomplished by friction fit or other securing means known to those in the art in order to retain the pivot 368 and fan 366 within the cover 316. The retention of the pivot 368 and fan 366 allows the cover 316 and fan assembly 318 to be removed from the base 314 as a single unit (see FIG. 12).

Referring now to FIGS. 9, 10 and 12-14, the various components of the drive mechanism 320 will be described. The drive mechanism 320 includes a plunger 406, a screw 408, a spring 410, a ratchet 412, and a ratchet cover 414. The plunger 406 comprises a circular button 416 and a cylindrical wall 418 depending from an underside 420 of the button 416 (see FIGS. 9 and 10). The cylindrical wall 418 of the plunger 406 is shaped to fit within the cylindrical support 356 of the covet 316. Hooks 419 that are disposed on a distal end of the cylindrical wall 418 interact With the cylindrical support 356 to prevent the plunger 406 from being removed from the housing 312. The screw 408 extends from the underside 420 of the button 416 within the cylindrical wall 418. When the plunger 406 is attached to the housing 312 the button 416 substantially covers the aperture 348 in the cover 316, which provides for a gap 421 between the button 416 and the cover 316 to allow air to enter the housing.

Figure 13:
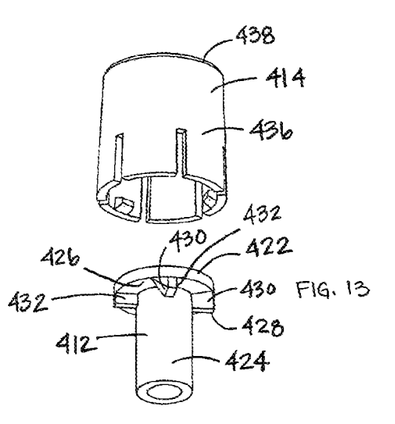
FIG. 13 is an exploded isometric view of a portion of a drive mechanism of the centrifugal fan device of FIG. 7.
Figure 14:
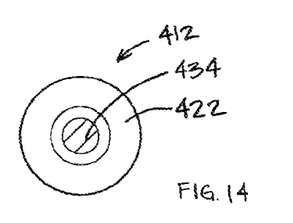
FIG. 14 is a plan view of a ratchet for use in the centrifugal fan device of FIG. 7.

As shown in FIGS. 13 and 14, the ratchet 412 includes a disc-shaped cap 422 and a cylindrical tube 424 depending from an underside 426 of the cap 422. A plurality of teeth 428 also depend from the underside 426 of the cap 422. The teeth 428 include sloped first sides 430 and vertical second sides 432. The teeth 428 on the ratchet 412 are designed to interact with the plurality of teeth 384 on the axle 378 of the centrifugal fan 366. As shown in FIG. 14, the ratchet 412 further includes a slot 434 within the cap 422, which is shaped to receive the screw 408 therethrough in a screw-type engagement to convert vertical movement of the plunger 406 into rotational movement of the fan 366.

Referring now to FIG. 13, the ratchet cover 414 includes a cylindrical body 436 having a closed top end 438. The ratchet cover 414 is designed to fit over the ratchet 412 and the axle 378 to retain the ratchet 412 in the housing 312 when the device 310 is assembled. An aperture 440 is disposed in the top end 438 of the ratchet cover 414 (see FIG. 9), which is designed to allow the screw 408 to pass through the ratchet cover 414 into the ratchet 412.

After assembly, the cover 316, the fan assembly 318, and the drive mechanism 320 may be inserted onto the base 314 as a single cover unit 442 (see FIG. 12). Removal of the cover unit 442 allows for access to the refill 326 for inspection or replacement. It is further contemplated that the base 314 may include an aperture 444 disposed in a sidewall 446 of the base 314 (see FIG. 9). The aperture allows a user to see whether a refill 326 has been inserted into the device 310, the level of liquid compound 330 left in the refill 326, or allows a user to view a color of the reservoir to indicate the type of compound 330 disposed within the refill 326 without removing the cover unit 442. Alternatively, the base 314 may be made of a transparent material in order to allow a user to view the refill 326 or the base 31.4 may be eliminated altogether and the refill 326 adapted to interact and be retained to the cover unit 442.

When the cover unit 442 and base 314 are combined, the plurality of fan blades 370 are disposed at, approximately the same height as the horizontal surface 334 of the permeable substrate 332. By connecting the plurality of blades 370 from above with the annular plate 374, and positioning the horizontal surface 334 of the permeable substrate 332 adjacent the bottom of the fan, a large amount of surface area of the horizontal surface 334 is exposed. The liquid compound 330 disposed within the refill 326 is wicked up through the plurality of wicks 336 into the horizontal surface 334 of the permeable substrate 332. In this passive state, the compound 330 evaporates from the horizontal surface 334 of the permeable substrate 332 and exits the device 310 through the plurality of vents 352 in the cover 316. The plurality of wicks 336 continually draw the liquid compound 330 into the horizontal surface 334 of the permeable surface 332 allowing the liquid compound 330 to be dispersed throughout the horizontal surface 334. The plurality of wicks 336 allow the liquid compound 330 to be dispersed around the horizontal surface 334 such that one area of the horizontal surface 334 does not include considerably more liquid compound 330 than other areas. The uniform dispersal of the liquid compound 330 around the horizontal surface 334 creates a uniform diffusion profile, such that similar amounts of the fragrance are evaporated from all areas of the horizontal surface 334 even in the passive state, thereby allowing the liquid compound 330 to be dispersed 360° around the device 310.

At any time, a user may activate the device 310 to release a greater amount of compound 330 by providing a downward force F on the plunger 406. Application of the force F on the plunger 406 causes the screw 408 to move vertically downward through the slot 434 in the ratchet 412, which causes the ratchet 412 to rotate in a first direction. Rotation of the ratchet 412 in the first direction causes the vertical sides 432 of the ratchet teeth 428 to engage with the vertical sides 388 of the axle teeth 384, thereby causing the fan 366 to rotate. The rotating fan 366 draws air into the housing 312 of the device 310 through the gap 421 between the button 416 and the cover 316 as identified by arrow A. The air thereafter enters the fan 366 through the gap 376 between the barrel 372 and the annular plate 374. The plurality of blades 370 forces the air over the horizontal surface 334 of the permeable substrate 332. Subsequent to passing over the horizontal surface 334 of the permeable substrate 332, the air is laden with the compound 330 and exits the housing 312 of the device 310 through the plurality of vents 352 in the cover 316. In the present embodiment, the air is exhausted from the vents 352 radially about a full 360° of the device 310. During this active state, an increased rate of the compound 330 is released from the device 310 as compared to the passive state. Additionally, similar to the passive state, in the active state there is a uniform diffusion profile such that similar amounts of the compound are evaporated from all areas of the horizontal surface 334 of the permeable substrate 332. In other embodiments the air may be exhausted from the vents 352 about only a portion of the device 310.

When the downward force F is removed from the plunger 406, the spring 410 biases the plunger 406 upwardly to the unactuated position. The upward movement of the plunger 406 causes the upward movement of the screw 408 through the slot 434 in the ratchet 412. This upward movement causes the ratchet 412 to rotate in a second opposite direction. When the ratchet 412 rotates in the second direction, the sloped Sides 430 of the ratchet teeth 428 are able to ride up and over the sloped sides 386 of the axle teeth 384, thereby allowing the ratchet 412 to rotate without causing the fan 366 to rotate.

Figure 16:
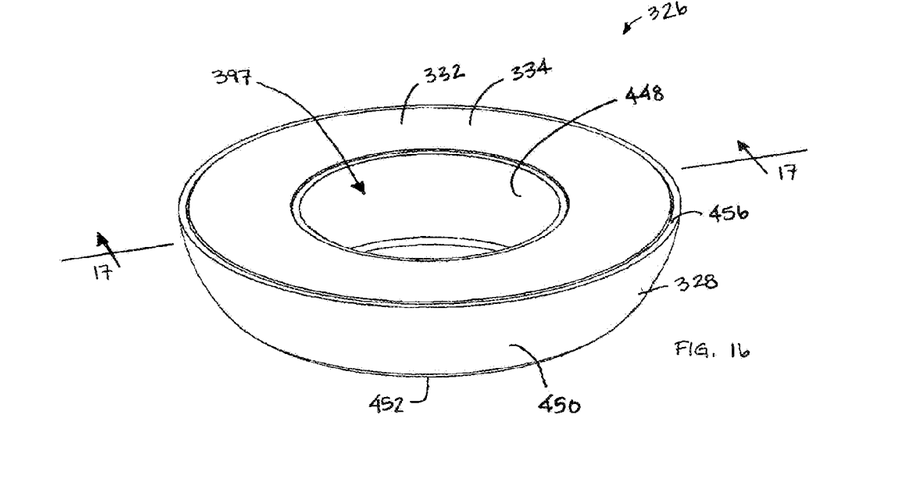
FIG. 16 is an isometric view of a refill for use in the centrifugal fan device of FIG. 7.
Figure 17:
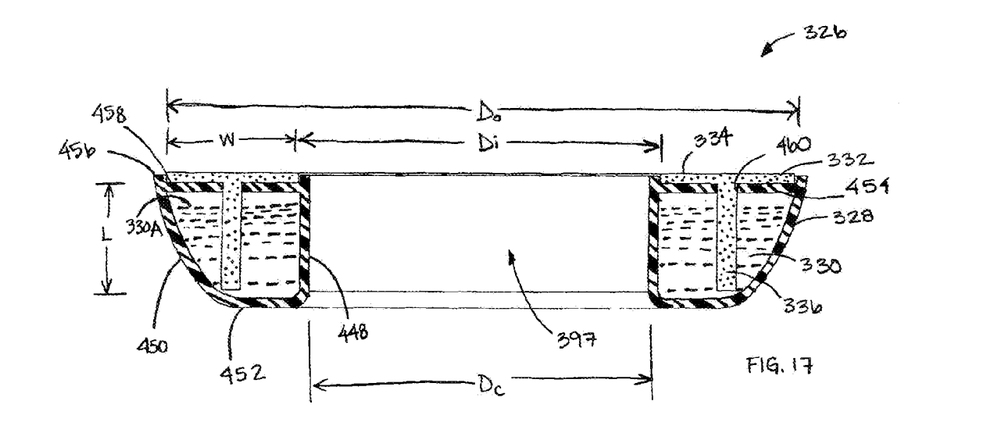
FIG. 17 is a cross-sectional view of the refill of FIG. 16 taken generally along the line 17-17 of FIG. 16.

Referring now to FIGS. 16 and 17, the refill 326 will be described with greater particularity. The reservoir 328 of the refill 326 has a generally U-shaped cross-section and includes inner and outer sidewalls 448, 450, respectively, and a bottom wall 452. In the present embodiment the reservoir 328 includes a top wall 454 that is integral with the inner and outer sidewalls 448, 450 to enclose the reservoir 328. However, in other embodiments the top wall 454 may be separable or entirely omitted. The top wall 454 is set below a top edge 456 of the reservoir 328 and defines a recess 458. In other embodiments, the top wall 454 is not recessed and may be flush with the top edge 456 or raised thereabove. The top wall 454 also includes a plurality of bores 460 disposed therein, which correspond with the plurality of wicks 336 as described below.

As shown in FIG. 17, the horizontal surface 3.34 of the compound permeable substrate 332 sits within the recess 458 such that the horizontal surface 334 is flush or substantially flush with the top edge 456 of the reservoir 328. The wicks 336 extending from the horizontal surface 334 extend through the bores 460 in the top wall 454 of the reservoir 328. In the present embodiment there are 4 wicks 336 and 4 bores 460, however, four or more wicks 336 and bores 460 may be used. For example, in one preferred embodiment, the refill 326 includes 4 to 10 wicks 336 and bores 460. The wicks 336 have a length L and the horizontal surface 334 has a width W. A ratio of the length L of the wicks 336 and the width W of the horizontal surface 334 is preferably between 0.5:1 and 1.5:1. More preferably the ration between L and W is between 0.8:1 and 1:1. In a preferred embodiment the wicks 336 extend to just above or are in contact with the bottom wall 452 of the reservoir 328, which allows the wicks 336 to stay in communication with the liquid compound 330 in the reservoir 328 as the compound 330 is used. The horizontal surface 334 of the annularly shaped permeable substrate 332 has an outer diameter $D_o$ and an inner diameter $D_i$. A ratio of the outer diameter $D_o$ and inner diameter $D_i$ of the permeable substrate is preferably between 2:1 and 1.5:1, and more preferably about 1.75:1. The central cavity 397 of the annular refill 326 has an inner diameter $D_C$.

Figure 18:
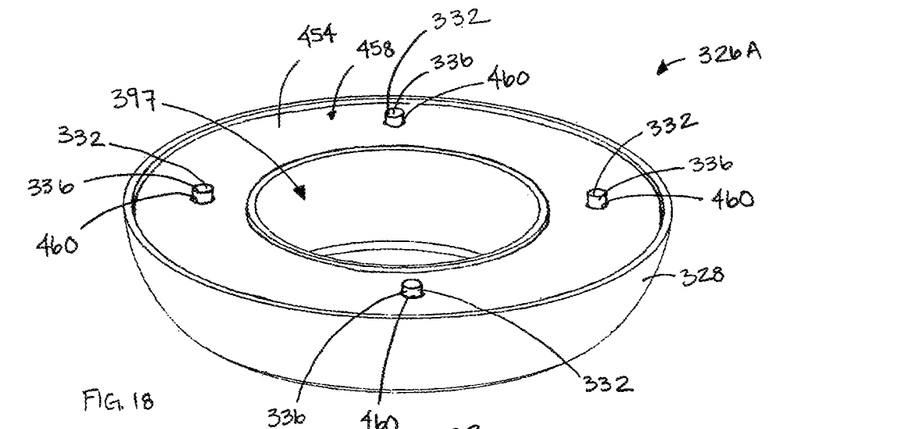
FIG. 18 is an alternative embodiment of a refill for use in the centrifugal fan device of FIG. 7.

Referring now to FIG. 18, in an alternative embodiment, the permeable substrate 332 includes only the plurality of wicks 336 extending through bores 460 in the top wall 454 of the reservoir 328. The wicks 336 allow the compound 330 to be wicked out of the reservoir 328 and into the air, which is then emitted passively or exhausted out of the device 310 when the fan 336 is activated. In particular embodiments, the wicks 336 may be positioned to a varying extent above the top wall 454 of the reservoir 328 to release more or less of the compound 330. Further, although the wicks 336 are shown centered and equidistant within the reservoir 328, the wicks 336 may be located anywhere within the reservoir 328 and top wall 454.

Figure 19:
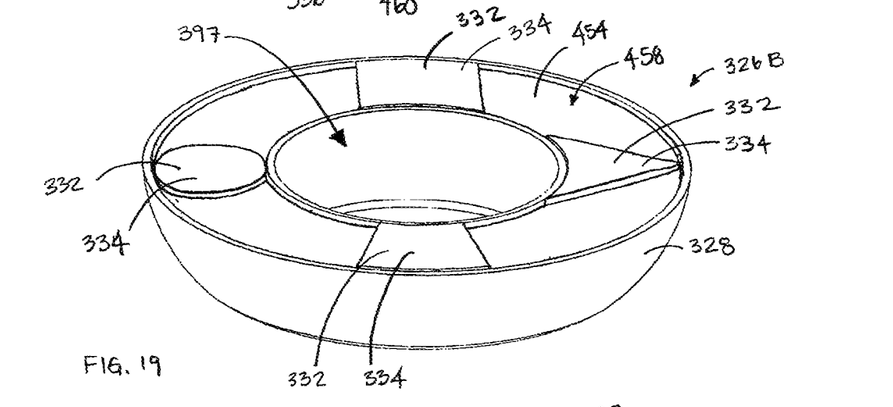
FIG. 19 is a further embodiment of a refill for use in the centrifugal fan device of FIG. 7.
Figure 20:
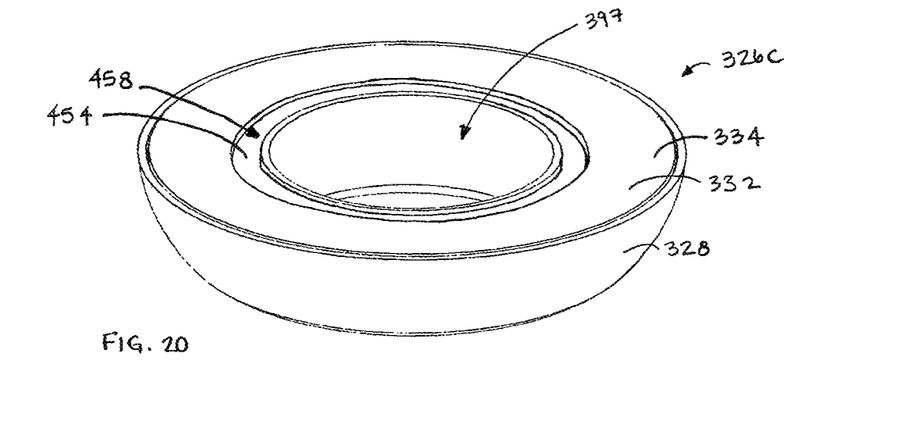
FIG. 20 is a still further embodiment of a refill for use in the centrifugal fan device of FIG. 7.

With reference to FIGS. 19 and 20, it is shown that the horizontal surface 334 of the permeable substrate 332 need not extend continuously around the reservoir 328 and may be designed to comprise other shapes than depicted in prior embodiments. For example, the horizontal surface 334 of the permeable substrate 332 may comprise a circle, a wedge, a triangle, a rectangle, or any other geometric shape that can rest on, or otherwise be disposed above, the top wall 454 of the reservoir 328 and provide adequate surface area for compound dispersal (see FIG. 19). Further, as shown in FIG. 20, the horizontal surface 334 of the permeable substrate 332 may be configured to cover only a portion of the annular top wall 454 of the reservoir 328.

The present centrifugal fan devices 10, 110, 310 provide features and advantages not found in prior art devices for delivering a fragrance or insecticide. For example, the combination of the centrifugal fan and its location adjacent the compound permeable substrate allow for better compound delivery, as compared to other known passive and/or heated devices.

A further advantage of the present centrifugal fan devices is that they allows for a small, more compact device, due to better air flow across the compound permeable substrate. As a result, the present centrifugal fan devices allow the compound permeable substrate to have a smaller surface area and require fewer wicks and/or allow for a reduction in the size of wicks, as compared with prior art devices, in order to achieve the same compound delivery to the environment of use.

An additional advantage of the present centrifugal fan devices is that they have less resistance to air flow, as a result of the present configuration forcing the air along the surface of the permeable member instead of against the surface, thus requiring a minimal amount of energy to operate and, therefore, prolonging battery life in the electronic devices, as compared with prior devices.

The exemplary embodiments disclosed herein are not intended to be exhaustive or to unnecessarily limit the scope of the invention. The exemplary embodiments were chosen and described in order to explain the principles of the present invention so that others skilled in the art may practice the invention. As will be apparent to one skilled in the art, various modifications can be made within the scope of the aforesaid description. Such modifications being within the ability of one skilled in the art form a part of the present invention and are embraced by the appended claims.

Other embodiments of the disclosure including all the possible different and various combinations of the individual features of each of the foregoing described embodiments and examples are specifically included herein.

INDUSTRIAL APPLICABILITY

Numerous modifications will be apparent to those skilled in the art in view of the foregoing description. Accordingly, this description is to be construed as illustrative only and is presented for the purpose of enabling those skilled in the art to make and use the invention and to teach the best mode of carrying out same. The exclusive rights to all modifications which come within the scope of the appended claims are reserved.

I claim:

1. A dispensing device, comprising:
a housing;
a fan;
an annular reservoir having a compound disposed therein; and
a permeable substrate in communication with the annular reservoir for releasing the compound in a first passive state, wherein the permeable substrate includes a horizontal surface and at least one wick extending from the horizontal surface into the reservoir, and wherein the compound is released from the permeable substrate according to a uniform diffusion profile, and
wherein rotation of the fan causes air to pass over the permeable substrate to release the compound in a second, active state.

2. The dispensing device of claim 1, wherein the horizontal surface is substantially parallel to a top surface of the compound.

3. The dispensing device of claim 1, wherein the fan is a centrifugal fan.

4. The dispensing device of claim 3 further including a drive mechanism in communication with the fan.

5. The dispensing device of claim 4, wherein the drive mechanism is manually operated by a plunger, wherein downward movement of the plunger causes the fan to rotate.

6. The dispensing device of claim 5, wherein upward movement of the plunger does not cause the fan to rotate.

7. A refill, comprising:
an annular reservoir having a compound disposed therein; and
an annular permeable substrate in communication with the compound,
wherein the permeable substrate includes a horizontal surface having at least one wick extending from the horizontal surface into the annular reservoir.

8. The refill of claim 7, wherein the horizontal surface is substantially parallel to a top surface of the compound.

9. The refill of claim 7, wherein a ratio of a length L of the at least one wick to a width W of the horizontal surface is about 0.5:1 to about 1.5:1.

10. The refill of claim 7, wherein the annular reservoir further includes inner and outer sidewalls, a bottom wall, and an annularly shaped top wall integral with the inner and outer sidewalls.

11. The refill of claim 10, wherein the top wall further includes at least one bore disposed therein.

12. The refill of claim 11, wherein the horizontal surface is disposed on the top wall and the at least one wick extends from the horizontal surface through the at least one bore into the annular reservoir.

13. The refill of claim 11, wherein four wicks extend from the horizontal surface through four bores into the annular reservoir.

14. A refill, comprising:
an annular reservoir having a compound disposed therein, wherein a plurality of wicks extend from the annular reservoir.

15. The refill of claim 14, wherein the annular reservoir includes inner and outer sidewalls, a bottom wall, and an annularly shaped top wall integral with the inner and outer sidewalls.

16. The refill of claim 15, wherein the plurality of wicks extend through a plurality of bores disposed in the top wall of the annular reservoir.

17. The refill of claim 16, wherein the plurality of wicks are in fluid communication with a horizontal surface.

18. The refill of claim 17, wherein the horizontal surface is substantially parallel to a top surface of the compound.

* * * * *